US006534528B1

(12) United States Patent
Bohn et al.

(10) Patent No.: US 6,534,528 B1
(45) Date of Patent: Mar. 18, 2003

(54) UTILIZATION OF POWDER PREPARATIONS CONTAINING HYDROXYPYRIDONES FOR TREATING LEG ULCERS AND DECUBITUS ULCERS

(75) Inventors: Manfred Bohn, Hofheim (DE); Karl Theodor Kraemer, Langen (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/600,903

(22) PCT Filed: Jan. 11, 1999

(86) PCT No.: PCT/EP99/00105

§ 371 (c)(1),
(2), (4) Date: Jul. 24, 2000

(87) PCT Pub. No.: WO99/37300

PCT Pub. Date: Jul. 29, 1999

(30) Foreign Application Priority Data

Jan. 24, 1998 (DE) .......................................... 198 02 708

(51) Int. Cl.$^7$ .......................... A61K 31/44; A01N 43/40
(52) U.S. Cl. ........................................................ 514/335
(58) Field of Search .......................................... 514/335

(56) References Cited

U.S. PATENT DOCUMENTS

| 2,540,218 A | | 2/1951 | Elliott N. Shaw |
| 4,797,409 A | | 1/1989 | Lohaus et al. |
| 4,906,648 A | * | 3/1990 | Minami et al. |
| 5,384,134 A | * | 1/1995 | Kross et al. |
| 5,494,658 A | | 2/1996 | Hänel et al. |

FOREIGN PATENT DOCUMENTS

| WO | WO 97/20560 | 1/1997 |

OTHER PUBLICATIONS

Lertzman et al., Drugs & Aging, 1996; 9(2): 109:121.*
Gennaro (editor), Remington: The Science and Practice of Pharmacy, 19th ed., 1995, p. 1413.*
"Leitlinen der Deutschen Gesellschaft für Phelbologie", Phlebologie 25–254–258(1996).
"Skin Integrity", pp. 1–13 (1989).
Derwent Abstract of WO 97/202560.

* cited by examiner

Primary Examiner—Sreeni Padmanabhan
Assistant Examiner—San-ming Hui
(74) Attorney, Agent, or Firm—Finnegan, Henderson, Farabow, Garrett & Dunner, LLP

(57) ABSTRACT

The inventive powder preparations containing at least one compound of formula (I) are suited for treating leg ulcers or decubitus ulcers.

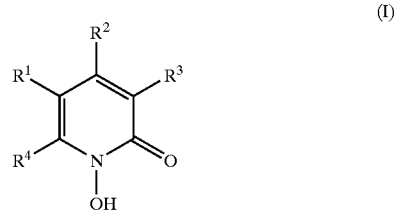

10 Claims, No Drawings

UTILIZATION OF POWDER PREPARATIONS CONTAINING HYDROXYPYRIDONES FOR TREATING LEG ULCERS AND DECUBITUS ULCERS

DESCRIPTION

This application is a national stage filing under 35 U.S.C. §371 of international application No. PCT/EP99/00105, filed on Jan. 11, 1999.

The use of hydroxypyridone-containing powder preparations for the treatment of leg ulcers and pressure ulcers.

The present invention relates to the use of a powder preparation containing hydroxypyridones for the treatment of leg ulcers (ulcus cruris) and pressure ulcers (decubitus ulcers).

The diagnosis of leg ulcers (ulcus cruris) is a collective term covering ulcers of varying origins (Phlebologie (1996); 25: 254–258). In Germany, about 1.6 million people are affected by poorly healing leg ulcers. The prerequisite for effective treatment of the ulcus cruris wound is to identify the possible causes of the development of the defect. It is possible to make the global statement of blood flow in the vessels of the lower leg is disturbed. The undersupply of the tissue with oxygen resulting from this leads to lesions, loss of tissue and finally necrosis and expansion of the defect. Infections with bacteria and fungi colonize the affected areas of skin and, in addition to enlarging the wound, also contribute to the formation of a very malodorous discharge.

The therapy of ulcus cruris consists of a dual strategy of local wound treatment and elimination of the causes of the ulceration. The latter may include compression therapy for an ulcer caused by chronic venous hypertension as well as rehabilitation of the arterial system for an arterial ulcus cruris.

It must always be taken into account in principle during local therapy of an ulcer that polypharmacy in use of the agents is avoided where possible because the patients often have multivalent contact allergies, in particular to ingredients of the local therapy which is sometimes applied to them for some years. The composition of local therapeutic agents should therefore be as simple as possible and the number of substances used should be kept as small as possible.

At present 2 treatment methods are accepted for local ulcer therapy, namely a phase-adapted and a phase-overlapping wound treatment.

These therapeutic policies relate to the 3 phases of wound healing, which take place as follows:

Exudation phase
(frequently triggered by superinfection of the ulcer)
Granulation phase
Epithelization phase Phase-adapted wound healing corresponds to the conventional, traditional therapy, must be continually changed and is elaborate but low-cost. Phase-overlapping therapy, which makes use of modern wound dressings with which treatment in the same way is possible in all 3 phases, is considerably simpler to manage but also considerably more costly. The two methods of therapy are comparable to one another in the therapeutic effect.

Phase-adapted wound treatment intervenes in the 3 phases of wound healing as follows:

Cleansing
Promotion of granulation
Promotion of epithelization through drying out The aim of cleansing is to produce a clean floor of the wound. For this it is necessary firstly to remove ointment residues and scabs and cut away any necroses present. The latter is best performed with a sharp spoon and with forceps and scissors. It is also possible to use enzymatic ointments which preferably degrade denatured protein. They contain substances such as trypsin, chymotrypsin, collagenase, fibrolysin, streptokinase etc. The surroundings of the ulcers should always be protected by applying hard zinc paste during this. Regular disinfection takes place in parallel with this, for example with potassium permanganate or Rivanol® baths.

Use of local antibiotics should be avoided because, on the one hand, resistance development and, on the other hand, the rate of sensitization is high. Granulation is promoted by mechanical stimulation. This is why curettage with a sharp spoon is still a very successful remedy. Somewhat milder stimulation of the floor of the wound is possible with sea sand, crystallized sugar or dextran powder. Hypertonic glucose and sodium chloride solutions also promote granulation. The treatments which were formerly customary with ointments, dyes and refined mineral oils are no longer recommended because on prolonged use they not infrequently lead to contact allergies.

The aim in the epithelization phase is to protect the sensitive newly formed tissue and promote epithelization. Epithelization starts when the granulation tissue has reached the upper level of the skin. Suitable as epithelization-promoting wound dressing are a number of products, for example hydrogels, hydrocolloids, foam compresses and gauze lattices. Transplantation of split skin can also be performed.

In phase-overlapping wound treatment for example dry wound dressings and gels (xerodressing and xerogel), and hydrocolloid wound dressings (hydrocolloid dressings) are used. They display their effect in each phase and can be employed as monotherapy for the treatment of ulcus cruris. Their properties include exudate retention, ulcer cleansing and promotion of granulation and epithelization.

According to publications from England, Denmark, Canada, Sweden, South Africa and the USA, 1 to 11% of all patients in hospitals had decubitus ulcers: the causation of this involves increasing life expectancy, the increase in patients at risk, and the fact that increasing numbers of extremely ill and seriously injured patients survive. Additional factors are the increasing shortage of nursing staff and the continuous overwork thereof.

Pressure maintained for a lengthy period on the skin with a disturbance of the microcirculation is the most important factor leading to a pressure ulcer (National Pressure Ulcer Advisory Panel (1989)). An important part is also played by shear forces acting on the skin and the underlying tissue, and friction and moisture. A decrease in patient mobility means more long-lasting stress on the skin at the same point. In the supine position, this is particularly the sacral region of the skin. Patients at particular risk of pressure ulcers are therefore elderly ones who are immobile, whose blood flow is impaired or who suffer from neurological disorders. Besides relieving the pressure on the affected areas of skin, the local treatment of decubitus ulcers is carried out in principle in the same way as for leg ulcers.

It has now been found that powder preparations of hydroxypyridone derivatives are extremely suitable for simple and cost-effective phase-overlapping local therapy of leg ulcers and pressure ulcers. This finding is surprising inasmuch as hydroxypyridone-containing preparations have to date been used exclusively as antimicrobial agents.

The invention therefore relates to the use of powder and at least one compound of the formula I

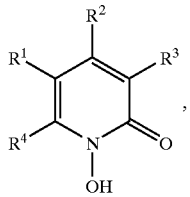

in which $R^1$, $R^2$ and $R^3$, which are identical or different, are hydrogen atom or alkyl with 1–4 carbon atoms, and $R^4$ is a saturated hydrocarbon radical with 6 to 9 carbon atoms or a radical of the formula II

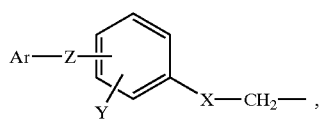

where

X is S or O,

Y is hydrogen atom or up to 2 halogen atoms such as chlorine and/or bromine,

Z is a single bond or the divalent radicals O, S, —$CR_2$—, in which R is hydrogen or $C_1$–$C_4$-alkyl, or other divalent radicals with 2–10 C and, where appropriate, O and/or S atoms linked in the form of a chain, it being necessary—if the radicals contain 2 or more O and/or S atoms—for the latter to be separated from one another by at least 2 C atoms, and it also being possible for 2 adjacent C atoms to be linked together by a double bond, and the free valencies of the C atoms being saturated by H and/or $C_1$–$C_4$-alkyl groups, Ar is an aromatic ring system which has up to two rings and which may be substituted by up to three radicals from the group of fluorine, chlorine, bromine, methoxy, $C_1$–$C_4$-alkyl, trifluoromethyl and trifluoromethoxy, for the production of a pharmaceutical for the treatment of leg ulcers and/or decubitus ulcers.

The term "saturated hydrocarbon radical" means that the radical can be straight-chain, branched or cyclic and contains no aliphatic multiple bonds. Examples of the $R^4$ radical are hexyl, heptyl, octyl, cyclohexyl or cycloheptyl.

The hydrocarbon radical $R^4$ in the compound of the formula I is preferably $C_6$–$C_8$-alkyl or cyclohexyl, which may also be linked via a methylene or ethylene group to the pyridone ring or may contain an endo-methyl group. $R^4$ may also be an aromatic radical which, however, is preferably linked via at least one aliphatic C atom to the pyridone residue.

The C chain members in the "Z" radicals are preferably $CH_2$ groups. If the $CH_2$ groups are substituted by ($C_1$–$C_4$)-alkyl groups, the preferred substituents are $CH_3$ and $C_2H_5$.

Examples of "Z" radicals are:

—O—, —S—, —$CH_2$—, —($CH_2$)$_m$— (m=2–10), —C($CH_3$)$_2$—, —$CH_2$O—, OCH$_2$—, —$CH_2$S—, —SCH$_2$—, —SCH($C_2H_5$)—, —CH=CH—$CH_2$O—, —OCH$_2$CH=CHCH$_2$O—, —OCH$_2$CH$_2$O—, —OCH$_2$CH$_2$CH$_2$O—, —SCH$_2$CH$_2$CH$_2$S—, —SCH$_2$CH$_2$CH$_2$CH$_2$O—, —SCH$_2$CH$_2$OCH$_2$CH$_2$O—, —SCH$_2$CH$_2$OCH$_2$CH$_2$OCH$_2$CH$_2$S— or —SCH$_2$C(CH$_3$)$_2$CH$_2$S—.

The "S" radical means a sulfur atom, and the "O" radical means an oxygen atom. The term "Ar" means phenyl and condensed systems such as naphthyl, tetrahydronaphthyl and indenyl, and isolated systems like those derived from biphenyl, diphenylalkanes, diphenyl ethers and diphenyl thioethers. The term "alkyl with 1 to 4 carbon atoms" means radicals such as methyl, ethyl, n-propyl, isopropyl, n-butyl, isobutyl or tertiary butyl.

Important representatives of the class of compounds characterized by formula I are:

6-[4-(4-chlorophenoxy)phenoxymethyl]-1-hydroxy-4-methyl-2-pyridone;

6-[4-(2,4-dichlorophenoxy)phenoxymethyl]-1-hydroxy-4-methyl-2-pyridone;

6-(biphenylyl-4-oxymethyl)-1-hydroxy-4-methyl-2-pyridone;

6-(4-benzylphenoxymethyl)-1-hydroxy-4-methyl-2-pyridone;

6-[4-(2,4-dichlorobenzyloxy)phenoxymethyl]-1-hydroxy-4-methyl-2-pyridone;

6-[4-(4-chlorophenoxy)phenoxymethyl]-1-hydroxy-3,4-dimethyl-2-pyridone;

6-[4-(2,4-dichlorobenzyl)phenoxymethyl]-1-hydroxy-3,4-dimethyl-2-pyridone;

6-[4-(cinnamyloxy)phenoxymethyl]-1-hydroxy-4-methyl-2-pyridone;

1-hydroxy-4-methyl-6-[4-(4-trifluoromethylphenoxy)phenoxymethyl]-2-pyridone;

1-hydroxy-4-methyl-6-cyclohexyl-2-pyridone;

1-hydroxy-4-methyl-6-(2,4,4-trimethylpentyl)-2-pyridone, 1-hydroxy-4-methyl-6-n-hexyl, -6-isohexyl-, 6-n-heptyl- or -6-isoheptyl-2-pyridone, 1-hydroxy-4-methyl-6-octyl- or -6-isooctyl-2-pyridone, in particular 1-hydroxy-4-methyl-6-cyclohexylmethyl- or 6-cyclohexylethyl-2-pyridone, it being possible for the cyclohexyl radical in each case also to carry a methyl radical, 1-hydroxy-4-methyl-6-(2-bicyclo[2,2,1]heptyl)-2-pyridone, 1-hydroxy-3,4-dimethyl-6-benzyl- or -6-dimethylbenzyl-2-pyridone or 1-hydroxy-4-methyl-6-(β-phenylethyl)-2-pyridone.

The abovementioned compounds of the formula I can be employed both in free form and in the form of salts; the use in free form is preferred.

The active ingredients of the compound of the formula I to be employed in the preparations can be prepared, for example, by processes disclosed in U.S. Pat. No. 2,540,218 or U.S. Pat. No. 4,797,409.

Powder preparations are particularly suitable for the use according to the invention of said compounds.

The active ingredient is incorporated into the preparations according to the invention in amounts which are normally between about 0.05 and about 5%, preferably between 0.1 and 1%.

It is possible with the pharmaceuticals according to the invention to achieve a thorough cure on local treatment of leg ulcers and decubitus ulcers.

Suitable as powder base are native substances such as sucrose, lactose, gelatin, pectin, carrageenan, agar, tragacanth and alginates, semisynthetic powder bases such as cellulose ethers, derivatives of starch, dextran and pectin, and completely synthetic substances such as polyvinylpyrrolidones. Modified starch types are particularly suitable. They are employed in amounts of from 95.0 to 99.4 parts by weight per 100 parts by weight of final product.

A further excipient suitable for the pharmaceutical preparation according to the invention is highly disperse silica to improve the flow and dusting properties.

The preparations are produced in a manner known per se by mixing the individual components and—where necessary—further processing adapted to the particular preparation.

The present invention is explained in detail by the following examples but is not confined to these. Unless otherwise noted, the stated amounts are based on weight.

EXAMPLE 1

A preparation according to the invention has the following composition:

| | |
|---|---|
| 6-Cyclohexyl-1-hydroxy-4-methyl-2(1H)-pyridone, 2-aminoethanol set | 1.00 g |
| Highly disperse silica | 0.01 g |
| Modified corn starch, phosphated | 98.99 g |

EXAMPLE 2

A preparation according to the invention has the following composition:

| | |
|---|---|
| 1-Hydroxy-4-methyl-6-(2,4,4-trimethylpentyl)-2(1H)pyridone | 0.50 g |
| Sucrose | 99.50 g |

EXAMPLE 3

A preparation according to the invention has the following composition:

| | |
|---|---|
| 6-[4-(4-Chlorophenoxy)phenoxymethyl]-1-hydroxy-4-methyl-2(1H)-pyridone | 0.25 g |
| Lactose | 99.75 g |

EXAMPLE 4

Activity Test

It was possible to show in a clinical study on patients with poorly healing leg ulcers that the ulcer area decreased by 80% after a treatment period of 6 weeks with the preparation according to Example 1 according to the invention. By comparison with this, the size of the wound decreased by only about 30% after standard therapy (hydrogen peroxide, potassium permanganate, sodium chloride solution).

What is claimed is:

1. A method for the treatment of a leg ulcer or a decubitus ulcer, wherein the ulcer is not infected, which comprises contacting the ulcer with a pharmaceutical which comprises a powder and at least one 1-hydroxy-2-pyridone of the formula I

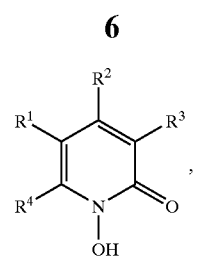

or a salt thereof,
where
$R^1$, $R^2$ and $R^3$, which are identical or different, are a hydrogen atom or alkyl with 1–4 carbon atoms, and
$R^4$ is a saturated hydrocarbon radical with 6 to 9 carbon atoms or a radical of the formula II

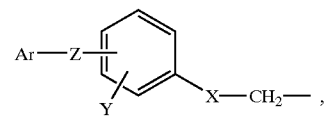

where
X is S or O,
Y is a hydrogen atom or up to 2 halogen atoms,
Z is a single bond or a divalent radical being O, S, —$CR_2$—, in which R is hydrogen or ($C_1$–$C_4$)-alkyl, or other divalent radical with 2–10 C and, optionally, O and/or S atoms linked in the form of a chain, wherein—if the radicals contain 2 or more O and/or S atoms—the latter are separated from one another by at least 2 C atoms, and it also being possible for 2 adjacent C atoms to be linked together by a double bond, and the free valencies of the C atoms being saturated by a hydrogen atom and/or ($C_1$–$C_4$)-alkyl groups,
Ar is an aromatic ring system which has up to two rings and which may be substituted by up to three radicals from the group of fluorine, chlorine, bromine, methoxy, ($C_1$–$C_4$)-alkyl, trifluoromethyl and trifluoromethoxy.

2. A method as claimed in claim 1, wherein Ar is a bicyclic system which is biphenyl, diphenylalkane or diphenyl ether.

3. A method as claimed in claim 1, wherein $R^4$ in the compound of the formula I is a cyclohexyl.

4. A method as claimed in claim 1, wherein $R^4$ in the compound of the formula I is an octyl radical of the formula —$CH_2$—$CH(CH_3)$—$CH_2$—$C(CH_3)_3$.

5. A method as claimed in claim 1, wherein the compound of the formula I is 1-hydroxy-4-methyl-6-[4-(4-chlorophenoxy)phenoxymethyl]-2-(1H)pyridone, 1-hydroxy-4-methyl-6-cyclohexyl-2-(1-H)-pyridone or 1-hydroxy-4-methyl-6-(2,4,4-trimethylpentyl)-2-(1H)-pyridone.

6. A method as claimed in claim 1, wherein the powder base comprises modified corn starch, sucrose, lactose or a mixture thereof.

7. A method as claimed in claim 1, wherein the pharmaceutical additionally comprises highly disperse silica.

8. A method as claimed in claim 1, wherein the 1-hydroxy-2-pyridone of the formula I is employed in an amount of about 0.05% to about 5%.

9. A method as claimed in claim 1, wherein Y is up to 2 halogen atoms, and wherein the halogen atoms are chlorine and/or bromine.

10. A method as claimed in claim 8, wherein the 1-hydroxy-2-pyridone of the formula I is employed in an amount of about 0.1% to about 1%.

* * * * *